US00PP11903P2

(12) United States Plant Patent
Glicenstein

(10) Patent No.: US PP11,903 P2
(45) Date of Patent: Jun. 5, 2001

(54) CHRYSANTHEMUM PLANT NAMED 'SPARKLING YOLAURIE'

(75) Inventor: Leon Glicenstein, State College, PA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/224,731

(22) Filed: Jan. 4, 1999

(51) Int. Cl.[7] ..... A01H 5/00
(52) U.S. Cl. ..... Plt./289
(58) Field of Search ..... Plt./289

(56) References Cited

U.S. PATENT DOCUMENTS

P.P. 9,818 * 3/1997 VandenBerg ..... Plt./289
4,616,099 * 10/1986 Sparkes ..... 47/58

OTHER PUBLICATIONS

UPOV–ROM, 2000/02, Plant Variety Database, GTI JOUVE Retrieval Software, citation for 'Sparkling Laurie'.*

Broertjes, et al., 1980, "A mutant of a mutant of a . . . Irradiation of progressive radiation—induced mutants in a mutation breeding programme with *Chrysanthemum morifolium,*" Euphytica, 29:525–530.*

Gosling, ed., 1979, "The Chrysanthemum Manual—6$^{th}$ edition", The National Chrysanthemum Society, London, Essex Telegraph Press, Ltd., pp. 329–336.*

Broertjes, et al., 1978, "Application of Mutation Breeding Methods in the Improvement of Vegetatively Propagated Crops", Elsevier Sci. Pub. Co., New York, pp. 162–175.*

Searle, et al., 1968, "Chrysanthemums the Year Round", Blanford Press, London, pp. 27–29, 320–327.*

Chan, 1966, "Chrysanthemum and rose mutations induced by X–rays", Am. Soc. Hort. Sci. Proc., pp. 613–620.*

Broertjes, 1966, "Mutation breeding of Chrysanthemums", Euphytica, 15:156–162.*

Dowrick, et al., 1966, "The induction of mutations in Chrysanthemum using X– and gamma radiation", Euphytica, 15:204–210.*

* cited by examiner

*Primary Examiner*—Howard J. Locker
(74) *Attorney, Agent, or Firm*—E. A. Whealy

(57) ABSTRACT

A distinct cultivar of Chrysanthemum plant named 'Sparkling Yolaurie', characterized by its uniformly mounded plant habit; decorative-type inflorescences that are about 4.2 cm in diameter; attractive bright yellow-colored ray florets; and numerous inflorescences per plant.

1 Drawing Sheet

BACKGROUND OF THE INVENTION

The present invention relates to a new and distinct cultivar of Chrysanthemum plant, botanically known as *Dendranthema grandiflora* and referred to by the cultivar name Sparkling Yolaurie.

The new cultivar is a product of a mutation induction breeding program conducted by the inventor in Fort Myers, Fla., and Salinas, Calif. The objective of the breeding program is to create new garden-type Chrysanthemum cultivars having with desirable inflorescence form and color and good garden performance.

The new cultivar originated by exposing unrooted cuttings of the Chrysanthemum cultivar Laurie (discloed in U.S. Plant Pat. No. 9,818) to X-ray radiation at a level of 1,750 rads in December, 1994. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Salinas, Calif. The cultivar Sparkling Yolaurie was discovered and selected by the inventor as a single flowering plant within this population in June, 1995. The selection of this plant was based on its desirable ray floret color.

Asexual reproduction of the new cultivar by terminal cuttings taken in a controlled environment in Salinas, Calif., has shown that the unique features of this new Chrysanthemum are stable and reproduced true to type in successive generations.

SUMMARY OF THE INVENTION

The cultivar Sparkling Yolaurie has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sparkling Yolaurie'. These characteristics in combination distinguish 'Sparkling Yolaurie' as a new and distinct cultivar:

1. Uniformly mounded plant habit.
2. Decorative-type inflorescences that are about 4.2 cm in diameter.
3. Attractive bright yellow-colored ray florets.
4. Numerous inflorescences per plant.

Plants of the new Chrysanthemum can be compared to plants of the parent cultivar Laurie. However, in side-by-side comparisons conducted by the Inventor under commercial practice, plants of the new Chrysanthemum differed from plants of the cultivar Laurie in the following characteristics:

1. Plants of the new Chrysanthemum are taller than plants of the cultivar Laurie.
2. Plants of the new Chrysanthemum have larger inflorescence discs than plants of the cultivar Laurie.
3. Plants of the new Chrysanthemum flower later than plants of the cultivar Laurie.
4. Ray floret color of plants of the new Chrysanthemum is bright yellow whereas ray floret color of plants of the cultivar Laurie are orange bronze.

BRIEF DESCRIPTION OF THE PHOTOGRAPHS

The accompanying photographs illustrate the overall appearance of the new cultivar.

The photograph at the top of the sheet comprises a side perspective view of a typical flowering plant of 'Sparkling Yolaurie'.

The photograph at the bottom of the sheet comprises a close-up view of typical inflorescences of the cultivar 'Sparkling Yolaurie'. These photographs show the colors as true as it is reasonably possible to obtain in colored reproductions of this type. Floret and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Leamington, Ontario, Canada, under conditions which approximate those generally used in commercial garden Chrysanthemum production. One rooted cutting was planted in a 15-cm container on Jul. 20, 1998 and plants were grown outdoors under natural season conditions. Measurements and numerical values represent averages for typical flowering containers.

Botanical classification: *Dendranthema grandiflora* cultivar Sparkling Yolaurie.

Commercial classification: Decorative-type garden chrysanthemum.

Parentage: Induced mutation of *Dendranthema grandiflora* cultivar Laurie, disclosed in U.S. Plant Pat. No. 9,818.

Propagation:

*Type*.—Terminal tip cuttings.

*Time to rooting*.—Seven to ten days with soil temperatures of 21° C.

*Rooting habit*.—Fine, fibrous and well-branched.

Plant description:

*Appearance*.—Perennial herbaceous decorative-type garden Chrysanthemum. Inverted triangle. Stems initially upright, then outwardly spreading giving a uniformly mounded appearance to the plant. Freely branching with lateral branches potentially developing at every node, when pinched, about 9 laterals develop.

*Plant height*.—About 31 cm.

*Plant spread*.—About 43 cm.

*Foliage description*.—Leaf arrangement: Alternate. Length: About 5.2 cm. Width: About 3.7 cm. Apex: Mucronate. Base: Attenuate to truncate. Margin: Palmately lobed, sinuses parallel to divergent. Texture: Upper surface sparsely pubescent; lower surface moderately pubescent. Veins prominent on lower surface. Petiole length: About 1.9 cm. Petiole diameter: About 2.5 mm. Color: Young foliage upper surface: 147A. Young foliage lower surface: Darker than 147B. Mature foliage upper surface: 147A. Mature foliage lower surface: 147B. Venation upper surface: 147A to 147B. Venation lower surface: 147B.

Inflorescence description:

*Appearance*.—Decorative-type inflorescence form with oblong to elongated spoon-shaped ray florets. Inflorescences borne on terminals above foliage, arising from leaf axils. Disk and ray florets arranged acropetally on a capitulum. One inflorescence per terminal with numerous inflorescences per plant, about 9 per lateral stem.

*Flowering response*.—Under natural season conditions, plants flower in early October in the Northern Hemisphere, about 88 days after planting, and flower for at least three weeks depending on weather conditions.

*Inflorescence bud (before showing color)*.—Height: About 6 mm. Diameter: About 6 mm. Phyllary color: Close to 141A.

*Inflorescence size*.—Diameter: About 4.2 cm. Depth (height): About 1.9 cm. Diameter of disc: About 2.5 mm.

*Ray florets*.—Shape: Oblong to elongated spoon. Length: About 2 cm. Width: About 6 mm. Apex: Dentate. Margin: Entire. Texture: Smooth, glabrous. Orientation: Initially upright, then horizontal. Number of ray florets per inflorescence: Typically more than 175. Color: When opening, upper and lower surfaces: 9A. Opened inflorescence: Upper surface: 9A to close to 5A. Lower surface: 5B to 5C.

*Disc florets*.—Shape: Tubular, apex dentate. Length: About 3 mm. Width: Apex: About 1 mm. Base: About 1 mm. Number of disc florets per inflorescence: Typically fewer than 15. Color: Immature: 154A. Mature: Apex: 9A. Mid-section and base: Greenish white.

*Peduncle*.—Aspect: Flexible, angled about 50° to the stem. Length: First peduncle: About 4.3 cm. Fourth peduncle: About 6.5 cm. Diameter: About 1.5 mm. Texture: Pubescent. Color: 146A.

*Reproductive organs*.—Androecium: Present on disc florets only. Anther color: 9A. Pollen: Scarce. Gynoecium: Present on both ray and disc florets.

Disease resistance: Resistance to known Chrysanthemum diseases has not been observed on plants grown under commercial production conditions.

Seed production: Seed production has not been observed.

It is claimed:

1. A new and distinct cultivar of Chrysanthemum plant named 'Sparkling Yolaurie', as illustrated and described.

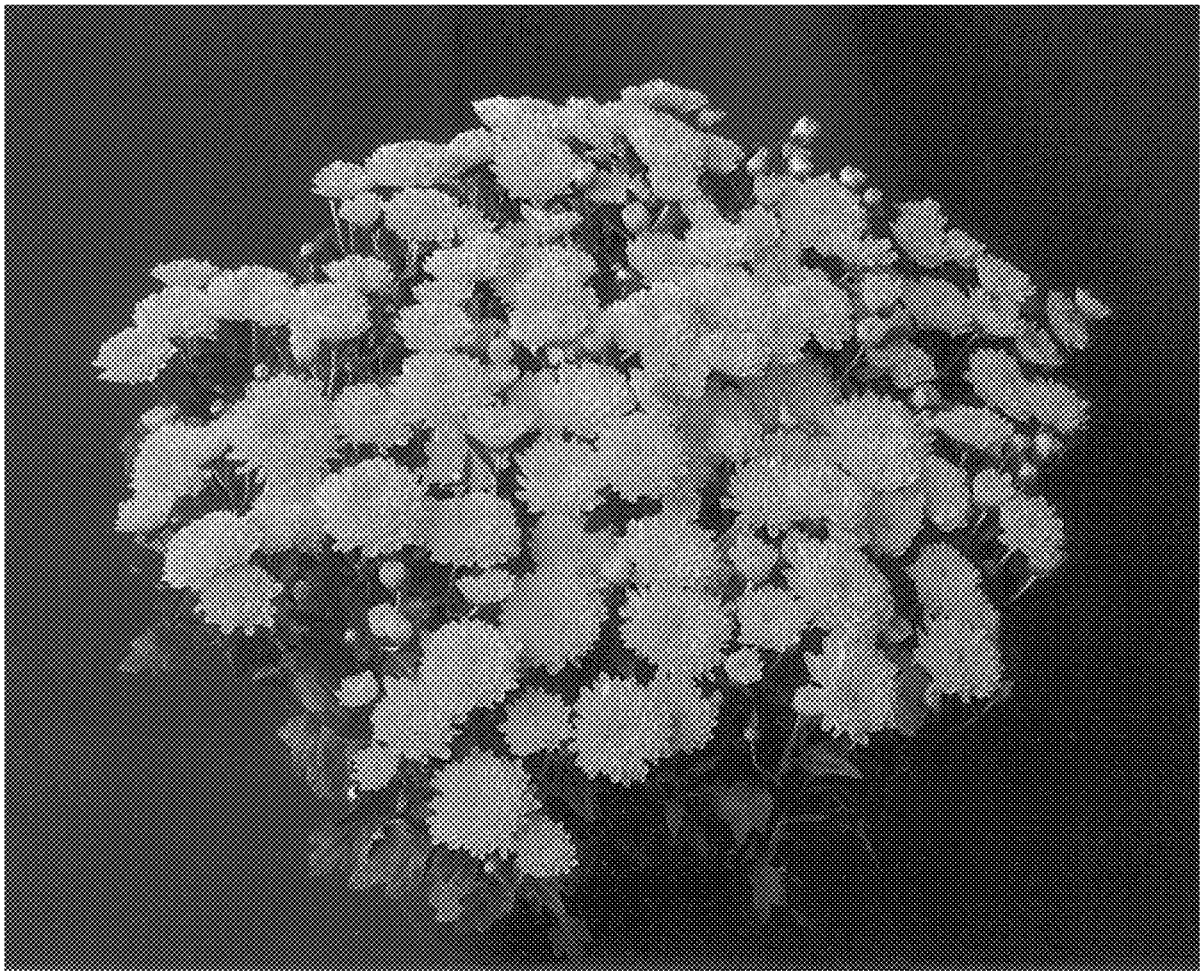
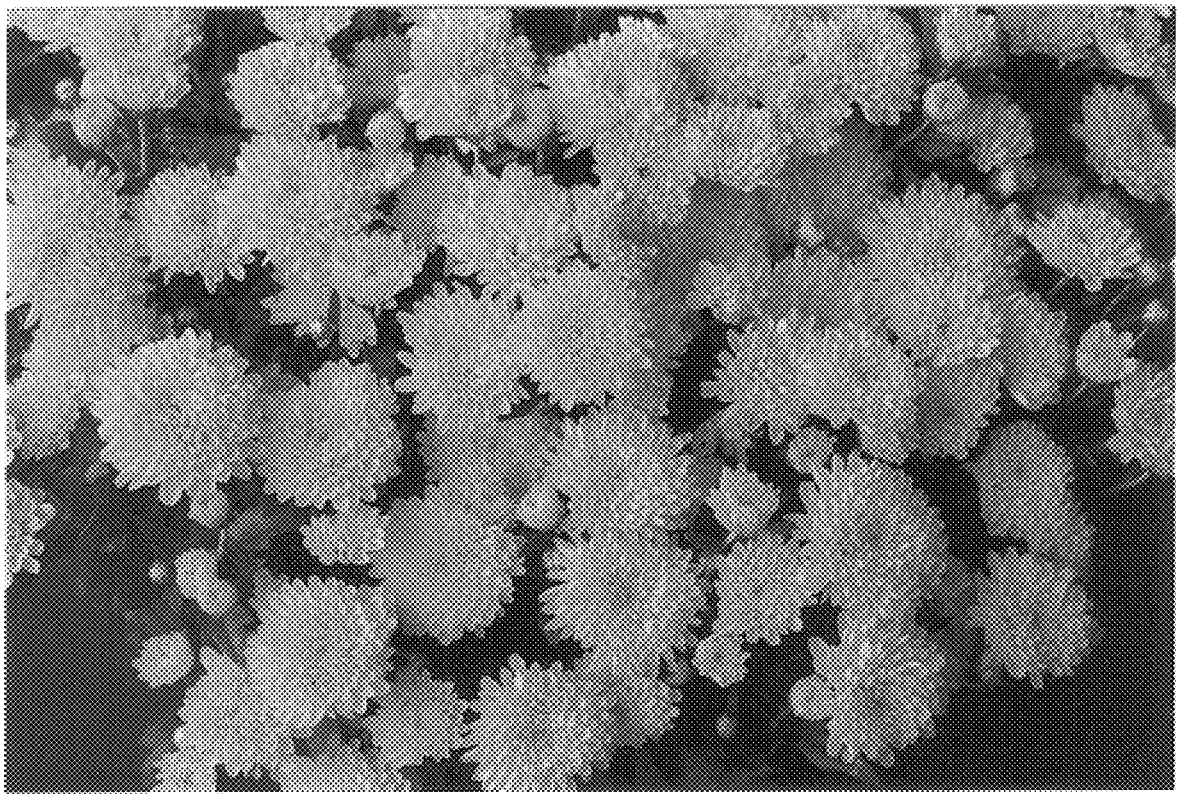

* * * * *